United States Patent [19]

Barabino et al.

[11] 4,217,415

[45] Aug. 12, 1980

[54] IMMOBILIZATION OF AN ENZYME SUBSTRATE

[75] Inventors: Raymond C. Barabino, Toledo; Melvin H. Keyes, Sylvania, both of Ohio

[73] Assignee: Technicon Instruments Corporation, Tarrytown, N.Y.

[21] Appl. No.: 886,504

[22] Filed: Mar. 14, 1978

[51] Int. Cl.² .................. C07G 7/02; G01N 31/14; G01N 31/08; C12D 13/04

[52] U.S. Cl. ...................... 435/98; 435/22; 435/99; 435/176; 435/178

[58] Field of Search ............ 195/31 R, 31 F, 31 P, 195/63, 68, 116, 103.55, 99; 252/430; 435/22, 95, 99, 176, 178, 98

[56] References Cited

U.S. PATENT DOCUMENTS

| | | | |
|---|---|---|---|
| 2,459,108 | 1/1949 | Lolkema | 260/209 |
| 2,626,257 | 1/1953 | Caldwell et al. | 260/233.3 |
| 3,208,918 | 9/1965 | Beers, Jr. | 195/116 X |
| 3,251,949 | 5/1966 | Lipps, Jr. | 195/31 P |
| 3,436,309 | 4/1969 | Ottinger et al. | 195/31 R |
| 3,912,590 | 10/1975 | Slott et al. | 195/31 R |
| 3,918,183 | 10/1975 | Johansson et al. | 195/63 X |
| 3,996,107 | 12/1976 | Martensson | 195/31 R |
| 4,033,820 | 7/1977 | Brouillard | 195/31 F X |
| 4,043,871 | 8/1977 | Blixt et al. | 195/68 X |
| 4,048,018 | 9/1977 | Coughlin et al. | 195/63 X |

OTHER PUBLICATIONS

Guilbault et al., Assay of Cholinesterase in an Electrode Systems with an Immobilized Substrate, Analytica Chim. Acta., vol. 85, 1976, pp. 295–306).

*Primary Examiner*—David M. Naff
*Attorney, Agent, or Firm*—S. P. Tedesco

[57] ABSTRACT

A carbohydrate substrate such as starch for a carbohydrate hydrolyzing enzyme is immobilized on a solid inorganic porous support to form a stable substrate-support composite useful in affinity chromatography and in methods where a precise amount of substrate is needed to perform an enzyme-substrate reaction to quantify the enzyme. The substrate may be activated with an agent such as cyanogen bromide or imidazole prior to deposition on the support so that it may be effectively modified while on the support. After deposition, the substrate is modified by reaction with an epoxyhalogen, aliphatic dihalide or aliphatic diamine to aid in holding it on the support. In an alternative embodiment, the carbohydrate, prior to deposition and modification on the support, is hydrolyzed with an enzyme, preferably dextranase.

8 Claims, No Drawings

IMMOBILIZATION OF AN ENZYME SUBSTRATE

BACKGROUND OF THE INVENTION

1. Field Of The Invention

This invention relates to a method of forming a stable composite of an enzyme substrate and a solid support. As known in the prior art much of clinical and biochemical separations methodology depends upon the size, shape and other physical characteristics of the material in question. This invention is concerned with the immobilization of carbohydrate enzyme substrates which may be used in affinity chromatography enzyme assay methodology or similar procedures.

2. Description Of The Prior Art.

In the past the importance of conditioning various biological materials for a particular use has been known. Small enzyme substrates have been immobilized (for example see "Assay of Cholinesterase In An Electrode System With An Immobilized Substrate" by Guilbault, G. G. and Iwase, A., Analytica Chimica Acta, V. 85, p. 295-300 (1976)). The particular enzyme substrate discussed herein, starch, has long been recognized as an important commercial product. Many procedures are known for the modification of starches for various functions. For example, U.S. Pat. No. 3,436,309, discloses a one-step process for the conversion of natural or so-called raw starch, to a product comprising a partially hydrolyzed, synthetic resin mixed complex which is used as a sizing for paperboards and the like.

Similarly, many procedures are known to hydrolyze starches, for example, U.S. Pat. No. 3,996,107, discloses a procedure to "liquify" starches under varying conditions with varying enzymes, and U.S. Pat. No. 3,912,590, which are formed by enzymatic hydrolysis at elevated temperatures to form a liquified product.

Also, starches, in granule form have been used to form medical dusting powders and the like. For example, U.S. Pat. No. 2,626,257, shows the use of starch granules for lubricating powders in medical gloves and the like. The patent also discloses that starch is treated with a diether forming halogen compound from either the halohydrin or epoxyhalohydrin groups, for example glycerol dibromo- and dichlorohydrins or epichloro-or epibromohydrin. This procedure produces from the raw ungelatinized starch a partially diether linked granular starch which can withstand harsh sterilization conditions without swelling or breaking. Therefore, the bridging groups are used in the procedure to retard granule swelling and so-called gelatinization. This material was not as flowable as desired and therefore the dry granules were mixed with various flow agents, for example non-hydroscopic metal oxides. Various other procedures for etherifying or esterifying starches are known, for example, U.S. Pat. No. 2,459,108.

Polysaccharides have also been used as support agents to provide for the immobilizing of various other chemical compounds. For example, U.S. Pat. No. 3,914,183, shows the use of a polysaccharide matrix to immobilize proteins containing free amino groups.

No method is believed known which form stable enzyme substrate composites using starch. These immobilized starch composites would find uses in affinity chromatography and in procedures where a precise amount of substrate is needed to perform an enzyme-substrate reaction to quantify the enzyme.

SUMMARY OF THE INVENTION

An object of the invention is to provide an immobilized carbohydrate enzyme substrate composite which is stable for long periods of time.

Another object of the invention is to provide a substrate composite which has the substrate modified to increse its affinity for the support and deposited onto a stable, water insoluble support.

The objects of the above invention are accomplished by forming an immobilized carbohydrate enzyme substrate composite by selecting a solid, substantially water insoluble support and depositing the enzyme substrate thereon. The enzyme substrate may be activated prior to deposition so that it may be more effectively modified onto the support. After deposition, the substrate is modified to aid in holding the substrate on the surface or in the pores of the support.

DETAILED DESCRIPTION OF THE INVENTION

The method and product of the present invention relates to the immobilization of carbohydrate enzyme substrates. Enzyme substrates that have great clinical significance are the carbohydrates, particularly the polysaccharides. These materials are an important storage form of sugars within humans and their condition and concentration within the body can be diagnostic of certain disease conditions.

A particularly important subclass of the polysaccharides are starches, which are used throughout this description to exemplify one type of polysaccharide substrate. Generally, starches are carbohydrate polymers or polysaccharides which are mixtures of amylose (a linear polymer of the sugar glucose) and amylopectin, another glucose polymer comprised of interlinked chains. The starch molecule is made up of repeating units of these structures joined by oxygen atoms, and it contains hydroxyl groups attached to the carbon skeleton. Starch occurs widely in plants and is particularly abundant in corn, potatoes, tapioca, and rice. It is formed by hydrolysis of cellulose and can itself be hydrolyzed to sugars with appropriate catalysts. A particularly effective class of catalysts which may be used to hydrolyze starches are the biocatalysts, enzymes. One very effective enzyme for starch hydrolysis enzyme is alpha-amylase. Starch is hydrophilic with warm water, forming stiff gels which are useful in finishing of fabrics, laundering, etc., and as thickening agents in food preparations, for example cornstarch. The starch-support composite of the present invention is particularly useful for use in the quantification of various enzymes. As pointed out above, one significant enzyme is alpha-amylase. It is known that alpha-amylase reacts with and breaks down starch molecules, but ceases at the $\alpha-1,6-$ glucosidic linkages or branched chain linkages. Thus, in some situations the immobilized starch may be useful in determining such enzymes. Accordingly, an immobilized starch substrate that would be very desirable in this invention would be one which has a high reaction rate with alpha-amylase, for example, the linear starch polymer mentioned above, amylose.

Based on experimentation with various starches, it was found that a starch high in this amylose type polysaccharide having mostly straight chains, and containing lower numbers of branched segments would be more suited for the starch substrate. Thus, a starch containing almost completely straight chain $\alpha-1,4-$ glucosidic linkages is preferable. However, the starch should also be capable of being hydrolyzed by enzymes such as alpha-amylase to produce oligosaccharides of the desired composition and length, for further analysis when the starch is being used only as an intermediate reactant in an analytical test. In addition, the starch should be free of materials which can cause competitive enzyme reactions to compete, or interfere with the hydrolysis of the starch by selected enzyme.

It has been found that wheat, corn and potato starches are among the starches which can be used as the starch substrate in this invention. Particularly preferred is potato starch because it is relatively inexpensive, can be obtained in high purity, resists clumping, has a high ratio of amylose to amylopectin, and contains 75-85% amylose. Potato starch in addition to having the above desirable properties for the starch substrate, is nearly totally hydrolyzed by enzymes such as alpha-amylase, producing oligosaccharides which are 2-6 monomers of glucose, with maltose being predominant. The properties and characteristics of the potato starch are well suited for the procedures of this invention and the high ratio of the amylose to amylopectin gives a long lifetime to the substrate reagent, and furthermore, higher yields of measurable glucose are seen in reactions with enzymes like glycoamylase.

Another use of the starch-support composite described above can be in affinity chromatography where various solution components are separated by their attraction to a particular substrate or other reagent. Many analytical procedures use polysaccharides and particularly starches, and thus the utility of the present invention is not limited to the examples set out above.

To form the immobilized substrate composite of the present invention the procedure is generally to weigh out a quantity of the support. The support is typically a refractory oxide powder, such as alumina, with the formula $Al_2O_3$. However, any similar, suitable refractory oxide powder, ceramic or the like will serve the purpose. In the average preparation about 20-80 grams of the support is weighed, washed and activated by standing under 2-6 N HCl for 2-15 hours. The support is thoroughly washed and may be stored under 0.05 molar acetate buffer at around pH 5.5.

A quantity of the preferred carbohydrate, herein starch, usually 3-200 grams depending upon the source and purity, is weighed out and suspended in 50-200 ml of buffer. If the starch is to be activated the activation is done while the starch is in this suspension or in solution if the starch is totally soluble. See the subsequent Examples 1, 2, 4 and 9 wherein the activating reagent or agent is cyanogen bromide or imidazole. While not being bound by any theory, it appears that the activating reagents form reactive centers on the starches, probably at the hydroxyl groups, which aid in the subsequent modifying of starch molecules to each other once the starch has been deposited by adsorption onto the support.

The support and starch are then combined and the starch is allowed to deposit onto the support and there interaction is strengthened by appropriate reagents. Thus, the resultant composite comprises starch molecules adsorbed to the surface of the support and then the starch molecules interact with each other via the additional reagents.

It has been found that members of the groups of epoxy-halogens, aliphatic dihalides and aliphatic diamines have been very useful in strengthening the interaction. Particularly useful examples of each group are epichlorohydrin, dibromoethane and diaminopropane, respectively.

A number of different mixtures and separate procedures have been found to be successful for forming starch support composites, depending on the type, source and purity of the starch. In some cases activated starch (using cyanogen bromide or imidazole as the reagent) is modified using epichlorohydrin alone. In other cases a mixture of agents is used, for example, a solution of 5 ml. methanol, 2 ml. dibromoethane, 1.5 ml. diaminopropane, 20 ml. distilled water and 0.5 ml. epichlorohydrin has been found to be very useful. Similarly, a solution of 10 ml. water, 10 ml. methanol, 0.25 ml. diaminopropane, 0.15 ml. dibromoethane and 0.1 ml. of 0.3 molar potassium hydroxide is suitable. The variety of mixtures is illustrated more fully in the examples and the necessary or desirable conditions are therein disclosed.

After deposition of the substrate on the support (where it is probably held to the support by adsorption) and modification of the substrate molecules to each other, the composite may be stored under a buffer e.g. 20 ml. of 0.01 molar acetate buffer at about pH 5.5, containing 0.05 molar potassium chloride with about a concentration of $10^{-5}$ molar sodium cyanide, as a bacteriostatic agent. An alternate buffer is 0.01 molar phosphate, at about pH 6.0 containing sodium chloride, calcium chloride, and a bacteriostat such as sodium cyanide or a trace of toluene.

In an embodiment of the invention where the substrate is a starch and is being used in an enzyme hydrolysis analysis, the starch is preferably immobilized on a porous support and packed into a cartridge through which the sample flows from an inlet port. The substrate is modified after deposition on the support, as above to form the immobilized composite. It was found that in enzyme hydrolysis analysis, at least about 0.25 grams of starch is preferred for continuous flow-through use for about two weeks.

The modification of substrate molecules after they are deposited on an inorganic support, particularly alumina, is preferred because a non-compressible support gives high flow rates for samples of unknown compounds when used in a flowing stream type of analyzer, thus consuming less time per analysis. This advantage also applies to uses in affinity chromatography where the support - starch - bound species composite may be easily physically isolated by pouring off the excess analysis fluid and washing the composite to isolate the bound species. The bound species is then desorbed to regenerate the support-starch composite for another use by altering the pH, ionic strength, etc. of the composite suspension.

In an alternative embodiment of the invention, the starch suspension may be subjected to a starch hydrolyzing enzyme prior to its adsorption or deposition onto the support. Dextranase is a preferred enzyme, as exemplified in Example 10. The starch hydrolyzing enzyme is believed to cleave the long, high molecular mass polysaccharide starch into smaller fragments, i.e. oligosaccharides. The shorter chains are believed to penetrate the pores of the porous alumina better than larger chains, and thereby increase the loading fraction of starch per gram of alumina.

The composition of the solid support is suitable as long as it is inert, dimensionally stable, and provides sufficient surface area, both inside the body of the support in the pores and cavities and on its exterior surfaces, for retention of the starch. When porous supports are used, they should be sufficiently porous and sorptive enough to retain enough starch to form a biologically active composite.

It has been found that the porous particles or the porous matrix having a volume porosity in the range of about 10 percent to 80 percent and preferably in the range of about 10-50 percent are quite suitable for the present purposes. The pore size of the support is important in that it should not be too small as to prevent immobilization of the starch or starch fragments therein. Similar considerations apply to any enzyme substrate being immobilized. Average pore size diameters of either fluid permeable membrane or porous particulates in the range of about 0.01 micron to 10 microns are suitable for most applications with about 0.01 to 2 being preferred for efficiency and economy.

As above, the porous particulate support can be refractory ceramic oxide powders such as alumina, zirconia, magnesia, silica, thoria, glass, powdered clay, powdered talc and the like. The particle size of the porous particulates is not critical although a size range of about $-5$ to mesh to plus 400 mesh is practical. Size fraction of about $-20$ to $\pm 100$ mesh (U.S. Standard Sieve) are preferably employed.

Porous, inert, rigid, dimensionally stable refractory fluid permeable membrane supports can be prepared by compacting such refractory oxide powders to form a "green compact" of the desired configuration. The green compacts are then fired for a time and at a temperature sufficient for sintering to yield porous, inert, rigid, dimensionally stable, fluid permeable refractory supports. The sintering should not be at a temperature or for a time which would cause collapsing or coalescence of the particles to form a non-porous body. A convenient indication of the degree of sintering is a comparison of the actual density of the fired compact as compared to the theoretical density of the oxide being fired. Of the many oxides which can be used for the present purposes, alumina is preferred for its chemical durability and ease of fabrication.

In forming the support from the powdered refractory oxide, the powdered particle size is selected to yield a sintered compact having a porosity and pore size in the range set forth above. The techniques for compaction and sintering of the porous supports are well-known in the art and form no part of the present invention. Suffice it to say that compacting pressures in the range of 1,000 psi to 10,000 psi and sintering temperatures in the range of 1,000° to 1,700° C. are commercially expedient. Additional details on compacting and sintering of refractory oxides can be obtained from the book "Oxide Ceramics" by E. Ryshkewitch, published in 1960 by Academic Press, New York, N. Y.

The porous matrix can also be made of a porous metal such as porous silver or porous stainless steel which can be in any geometric shape such as rods, cylinders, discs, plates, bars, and blocks and the like.

While refractory oxide powders are favored, other materials are contemplated to be used for the immobilization of enzyme substrates, for example natural and synthetic fibers such as polyethylene and polypropylene, wool, nylon, rayon, polyesters, acrylics. Also contemplated are inorganic fibers such as glass, carbon, asbestos fibrous ceramics, and metals, such as copper and stainless steel. The diameter of the separate fibers and their woven or packed arrangement can be varied. For example, a gauze of wire could be used which could be placed in a flow-through cell as an insert, act as a support, and then be easily removed and replaced.

Having described the invention and its construction generally the following specific examples and assay procedures for the resultant composite are given. For convenience in disclosure, all patent documents and publications mentioned herein are incorporated by reference.

EXAMPLE 1

Fifty grams of 40+50 mesh (0.1 micron-average pore diameter) alumina is washed under four liters one-tenth normal hydrochloric acid, followed by five liters distilled, deionized water. This washed alumina is then placed under nine normal hydrochloric acid for at least fifteen hours at zero to six degrees centigrade. Then wash the alumina under two aliquots, five hundred milliliter each with a five-hundredths molar acetate buffer, pH 5.6. Then the alumina is placed under two hundred to two hundred fifty milliliters of the same buffer, and aspirated on the vacuum line until no further bubbling occurs. This material is then placed under one hundred milliliters of acetate buffer, and allowed to swirl for one-half hour.

One to three grams of the carbohydrate amylose (95% pure from potato); is weighed out, and suspended in one-hundred milliliters of a pH 8.5, THAM-acid maleate buffer. Stir at least one-half hour with a magnetic stirrer, then add ten ml concentrated hydrochloric acid, wait two hours and add ten additional milliliters of concentrated hydrochloric acid, and stir overnight at room temperature.

On the next day the starch suspension is mixed with alumina solution, and stirred with an overhead stirrer for two hours. The pH is adjusted to eleven with sodium hydroxide pellets. Then fifteen-hundredths gram of cyanogen bromide is added to this mixture, the pH is maintained at eleven by the addition of seven normal sodium hydroxide, if necessary.

After five minutes, add the following modifying solution to the starch-alumina-CNBr mixture (allowed to react at least ten minutes): ten milliliters methanol, one-half (0.50) milliliter diaminopropane, and one-tenth milliliter dibromoethane. The modifying solution should be added all at once, and the reaction should proceed overnight while being stirred vigorously.

Then the supernatant is decanted off, and the final product is washed as outlined below:
(a) One liter, one-tenth normal hydrochloric acid,
(b) One liter distilled, deionized water,
(c) One liter five-hundredths molar acetate buffer,
(d) Repeat b,
(e) Repeat b, and
(f) Repeat c.

The alumina-starch composite is then stored under ten to thirty milliliters of five-hundredths molar acetate buffer, pH 5.6. The final product is then refrigerated at zero to four degrees centigrade.

EXAMPLE 2

Thirty grams of $-40+50$ mesh porous alumina having an average pore diameter of one-tenth micron is weighed out. The alumina is then washed under two liters of five-tenths molar hydrochloric acid. The washed alumina is then placed under two-hundred milliliters of six normal hydrochloric acid for one-and-a-half hours. At the end of this time, the now acid-activated alumina is then washed under five-hundred milliliters of one-hundredth molar acetate buffer, pH 5.6. The supernatant is then decanted off. The resulting product is then placed under one-hundred milliliters of one-hundredth molar acetate buffer, pH 5.6. This mixture is then placed on the laboratory shaker, at room temperature, for one-half hour, and is brought to pH eleven with six normal sodium hydroxide.

Five gram of the carbohydrate, starch (80–95% amylose from potato) is completely suspended in seventy-five milliliters of one-hundredth molar acetate buffer, pH 5.6, for at least two hours. To the amylose-buffered suspension is added sufficient sodium hydroxide to bring the pH to ten-and-a-half to eleven-and-a-half. This mixture is allowed to equilibrate at room temperature for at least one-half hour.

To the resulting mixture is added four grams of cyanogen bromide. The pH of the mixture is maintained between ten-and-a-half and eleven until all the cyanogen bromide has dissolved, or the pH remains constant. The resulting mixture is allowed to react one-half hour, while swirling on the laboratory shaker at room temperature.

In the meantime, fifteen-hundredths milliliter of diaminopropan and twenty-hundredths milliliter of dibromoethane is dissolved in five milliliters of methanol. Then, this mixture is added to the cyanogen bromide activated starch, acid-activated porous alumina mixture.

This final mixture is allowed to react for one additional hour. The supernatant is decanted off. The resulting product is then washed with:

(a) One liter five-tenths molar ammonium sulfate, enzyme grade,
(b) One liter distilled, deionized water, and,
(c) Five hundred milliliters, one-hundredth molar acetate buffer, pH 5.6. The now washed alumina-starch composite is then stored under ten milliliters of acetate buffer (0.01 M, pH 5.6), under refrigeration at zero to four degrees centigrade.

EXAMPLE 3

Fifty-four grams of −40+50 mesh porous alumina (porosity: 35%, average pore size: 0.1 micron) is washed under five-tenths molar hydrochloric acid until free of fines. The alumina is then placed under two hundred milliliters nine normal hydrochloric acid, for one-and-a-half hour. At the end of this time the alumina is washed under five-hundredths molar acetate buffer, pH 5.5.

After the acetate wash, the alumina is placed under one hundred milliliters of distilled, deionized water, brought to alkaline pH with ten to twenty grams seven normal sodium hydroxide. The mixture is allowed to swirl on the laboratory shaker for one-half (0.5) hour.

Prepare a ten to twenty percent amylose (practical grade) suspension in seventy-five percent phosphoric acid allow to stir for one-half hour.

During this time a modifying solution is prepared as follows:

(a) Five milliliters of methanol.
(b) Two milliliters of dibromoethane.
(c) One-and-a-half milliliters of diaminopropane.
(d) Twenty milliliters distilled, deionized water, and
(e) One-half milliliter to epichlorohydrin.

The amylose suspension is then added to the acid-alumina suspension. Into this mixture the modifying solution is slowly added over a one-half hour period. The reaction is then allowed to proceed for at least fifteen hours at room temperature.

The supernatant is decanted off, and the product is washed under acetate buffer (0.05 M, pH 5.6), salt (0.05 M NaCl, 0.05 M CaCl$_2$), and three to five liters of distilled, deionized water.

The composite is then stored at zero to four degrees centigrade under twenty to thirty milliliters of acetate buffer (0.05 M, pH 5.6).

EXAMPLE 4

Fifty-three grams of −40+50 meshed porous alumina (average pore diameter; one-tenth (0.1) micron; porosity: 35%) is washed until free of fines and acid-activated under nine normal hydrochloric acid for one-and-a-half hours. The mixture is then evacuated of air by aspiration for about ten minutes, and placed under fifty to one hundred milliliters of 0.01 molar acetate buffer at about pH 5.6 milliliters of 0.01 molar acetate.

To a four to ten percent, fifty milliliter sample of the carbohydrate amylose (practical grade from potato) suspension is added sufficient concentrated phosphoric acid to make the suspension at least seventy-five percent in phosphoric acid. To this mixture is added seventy-five milliliters of distilled deionized water. After about three hours, the mixture is brought to pH eleven-and-a-half with seven normal sodium hydroxide. After one-half hour, two grams of cyanogen bromide is added, and the pH is maintained at eleven until all the cyanogen bromide is dissolved or there is no further change in pH. The reagents are allowed to react for one hour.

Meanwhile, the acid-activated alumina is washed under distilled, deionized water until free of fines. The cleaned alumina is placed under one hundred milliliters of distilled, deionized water, made alkaline by the addition of twenty to fifty milliliters of sodium hydroxide. To this alkaline mixture is added the activated starch. The resulting mixture is allowed to stir for one-half hour.

During this time, a modifying solution is prepared, as in Example 3. At the end of the one-half hour during which the alumina-amylose mixtures were allowed to stir, the modifying solution is quickly added. The reaction is allowed to continue for at least fifteen hours.

EXAMPLE 5

Seventy-five grams, −40+50 mesh (average pore diamter 0.1 micron) porous alumina is weighed out. The alumina is then acidified under three normal hydrochloric acid for two-and-a-half hours. This mixture is then evacuated of air by aspiration for about ten minutes. After which, the alumina is carefully washed with distilled, deionized water, and is placed under fifty to one hundred milliliters of one-hundredth molar acetate buffer, pH 5.6.

Two grams of amylose is suspended in fifty milliliters of one-hundredth molar acetate buffer, pH 5.6. After one-half hour of stirring, the starch suspension is added to the alumina, and is allowed to swirl undisturbed an additional one-half hour.

During this time a modifying solution is prepared by mixing twenty milliliters of methanol one-half milliliter of diaminopropane three-tenths milliliter of dibromoethane three-tenths milliliter of concentrated hydrochloric acid and ten milliliters of one-hundredth molar acetate buffer, pH 5.6.

To the amylose-alumina suspension the modifying solution is added. The material is allowed to react overnight (about fifteen hours) at room temperature, while swirling on the lab shaker. The product is washed as in Example 3.

EXAMPLE 6

Fifty-three grams of $-40+50$ mesh porous alumina is weighed out. This alumina is washed, and acid activated as in Example 2, and washed with distilled, deionized water until free of fines.

A stock suspension is prepared as in Example 7, and twelve grams of potassium hydroxide pellets are added, and allowed to dissolve. Then twenty-five grams of potassium sulfate is added, and allowed to dissolve.

To the clean acid-activated alumina is added the soluble amylose, which is then allowed to equilibrate for at least one-half hour, under alkaline pH. To this mixture is added sixteen and seven-tenths milliliters of epichlorohydrin. The reaction is allowed to proceed for at least fifteen hours. The final product is washed and stored as in Example 7.

EXAMPLE 7

Forty-five grams of porous $-40+50$ mesh alumina, having an average pore diameter of one-tenth micron is weighed out, re-screened, washed, until free of fines and dried as in Example 1. This alumina is then placed under two hundred milliliters of distilled, deionized water. This alumina-water mixture is allowed to stir 15 minutes.

At the end of this time, twenty-five grams of potassium sulfate is added, and is allowed to stir until completely dissolved. Then, to this mixture is added six grams of potassium hydroxide and is allowed to stir until dissolved.

Then fourteen grams of amylose (practical grade) is added to the mixture gradually over a one-half hour period to ensure complete mixing of the reagents. After this time ninety-one hundredths milliliter of epichlorohydrin is added, and the mixture allowed to react as least fifteen hours, at room temperature, under constant agitation.

The next day the supernatant is decanted off. The aluminaamylose composite is washed under one to three liters of distilled, deionized water. The washed product is then stored under one-tenth molar acetic acid, and is one-hundredths molar in sodium chloride, and five-hundredths molar calcium chloride dihydrate. The preparation is then refrigerated at zero to four degrees centigrade until ready for use.

EXAMPLE 8

Forty-five grams of porous (35%), $-40+50$ mesh alumina having an average pore diameter of one-tenth micron, is weighed out. The alumina is rescreened, washed, and dried for at least ten hours at two hundred degrees centigrade. This alumina is then placed under six normal hydrochloric acid for no more than two hours.

The acid is decanted off. The now acid-activated alumina is placed under two hundred milliliter of distilled, deionized water, and stirred. The stirrer is turned to a medium speed. To the stirring alumina-water suspension is added twenty-five grams of potassium sulfate and five grams of potassium hydroxide pellets.

After the potassium sulfate, and potassium hydroxide has dissolved, sixty grams of amylose is added. One hundred additional milliliters of distilled, deionized water is added. Gradually, during one-half of vigorous stirring with the overhead stirrer forty additional grams of amylose is added to the mixture. Concurrently, two hundred twenty-five milliliters of distilled, deionized water is also added. After these reagents have been completely added, the resulting mixture is allowed to stir vigorously an additional twenty minutes.

At the end of this time, four milliliters of epichlorohydrin is added to the alumina-amylose mixture. The resulting mixture is allowed to react overnight (at least fifteen hours), at room temperature while stirring vigorously.

On the next day ten to fifteen milliliters of concentrated hydrochloric acid is added. The mixture is allowed to stir one-half hour.

The supernatant is decanted off. The final product is washed under eight to ten liters of distilled, deionized water. The product is stored as in Example 5.

EXAMPLE 9

Seventy-five grams of porous alumina is weighed out, washed, and acidified as in Example 2. This alumina is then rewashed under distilled deionized water until free of fines. Then it is placed under one hundred milliliters of one-hundredth molar acetate buffer, pH 5.6 (0.005 M in KCl), and evacuated of air bubbles under aspiration. Then it is placed under one hundred milliliters of the same buffer, and set aside for the moment.

One-and-a-half grams of amylose from potato is suspended in two hundred milliliters of the same buffer, and allowed to stir about one hour. To the amylose is added three grams of imidazole. The resulting mixture is allowed to stir vigorously, at least fifteen hours, at room temperature.

The next day the starch suspension is added to the alumina mixture, and is allowed to equilibrate for two hours.

During this time the following modifying solution is prepared: twenty milliliters of methanol, one-half milliliter of diaminopropane, one-quarter milliliter dibromoethane, two-tenths milliliter concentrated hydrochloric acid, and ten milliliters distilled deionized water. This modifying solution is added all at once to the starch-alumina mixture. The reaction is allowed to proceed overnight, at room temperature, while being vigorously mixed in the laboratory shaker.

The final product is washed by swirling under, 200 ml aliquots, of 3 liters of distilled, deionized water. The final product is then stored under 10-20 mls of 0.01 M acetate buffer, pH 5.6, containing 0.05 M KCl, with $1 \times 10^{-4}$M NaCN as a bacteriostat. It is refrigerated at 0–5° C. until ready for further use.

EXAMPLE 10

Forty-five grams porous alumina is weighed out, washed until free of fines, and placed under one hundred milliliters overnight (about fifteen (15) hours at room temperature) of water.

Five grams of soluble starch is dissolved in one hundred milliliters, of one millimolar phosphate buffer, pH 6.0. Stir for twenty minutes, at room temperature. Ten to fifteen grams of immobilized dextranase is added to the soluble starch. The resulting mixture is kept for about 15-18 hours at room temperature, after being covered with parafilm.

The next day the soluble starch is separated from the insoluble dextranase, and is added to the washed acid-activated alumina, to which the following modifying solution is added:

(a) Twenty-five hundredths of a milliliter of diaminopropane.
(b) Ten milliliters of methanol,
(c) One-tenth milliliter, three-tenths molar potassium hydroxide,
(d) Fifteen hundredths milliliter dibromoethane, and
(e) Ten milliliters of distilled, deionized water.

The mixture is then allowed to react overnight at room temperature, on the laboratory shaker at high speed. Washing and storage of the final product is as in Example 5.

THE ASSAY OF INSOLUBLE STARCH

There are two methods used for the determination of the amount of grams of starch bound per gram of alumina. They are; (1) $I_2$ adsorption, and (2) gravimetric. While the gravimetric procedure is preferred, due to its lower incident of interference, both procedures have been used reliably.

FORMULA

Optical Density, 340 nm of $I_2$ = gm Starch/gm $Al_2O_3$, where N varies from 10 to 16, $N_{avg.}$ = 12. N seems to be a function of the length of time the alumina-starch composite is fired at 1000° C.; i.e., N = 12, t = 3 hrs,
N = 14, t = 10 hrs., and
340 nm = absorbance wavelength.

EXAMPLE 11

DETERMINATION OF THE AMOUNT OF STARCH

Insolubilized By A Semiquantitative Iodine Adsorption Method

To an aliquot of alumina-starch composite in 25 ml of buffer, was added 1.0 ml of a 0.1 N $I_2$ stock solution. A control was determined containing blank activated alumina, which did not absorb $I_2$ from the solution. The absorbance is measured as quickly as possible in the visible region, at 340 nm. The moles of $I_2$ present are determined from the stiochiometric relationship:

$C_A V_A = C_B V_B$, where:
$C_A$ is the concentration of the stock $I_2$ solution,
$V_A$ is the volume aliquot of stock $I_2$,
$V_B$ is the volume of the assay medium, and
$C_B$ is the concentration of $I_2$ in the assay medium.

This value is subtracted from the control value, the difference being the $I_2$ adsorbed by the bound starch. This difference is then correlated to the percent starch by a calibration curve. The starch-alumina composite is then dried and weighed. The percent starch is divided by this weight and multiplied by the density of the alumina, 2.6. The units are percent starch per ml alumina-starch composite. The starch content is then estimated by dividing this value by 100 to yield a value having units of grams of starch/ml alumina-starch composite. This method is semi-quantitative because there exists two equilibrium conditions:

(1) $I_2 \rightarrow 2I^-$, and (2) $I^- + $ starch $\rightarrow$ starch $- I^-$ complex.

Determined by measuring the difference in adsorbance between a control, and standard starch solutions having the same concentration of $I_2$, then plotting this absorbance versus the percent starch in the standard solution.

EXAMPLE 12

DETERMINATION OF THE AMOUNT OF STARCH

Insolubilized By A Gravimetric Technique

A small aliquot of the alumina-starch composite is taken out of the bulk preparation, and placed in a preweighed crucible. The crucible with the sample is then dried overnight at 110° C. Then the dried crucible-sample is reweighed. Next, the crucible with its contents is placed in a furnace at 1000° C. for three (3) hours. After being allowed to cool to room temperature it is weighed again. Thus, the following measurements have been made;

Weight of crucible and 110° C. dried sample (gm) = A
Weight of crubicle and 1000° C. fired sample (gm) = B
Weight of crucible (gm) = C.

The grams of starch per gram of alumina is then the ratio of (A-B)/(B-C)

In accordance with the provisions of the patent statutes, the principle and mode of operation of the invention have been explained, and we have illustrated and described in the typical embodiment what is considered its best embodiment. It is understood that, within the scope of the appended claims, the invention may be practiced otherwise then as specifically illustrated and described in the typical embodiment and accompanying alternatives herein.

What is claimed is:

1. A method for forming an immobilized starch enzyme substrate-support composite comprising the steps of adding an immobilized starch hydrolyzing enzyme to a starch suspension, and allowing said enzyme to react with said starch to form starch fragments in said suspension, then removing said enzyme from said suspension, and forming a suspension of a solid, inert, inorganic, substantially porous support, then depositing said starch fragments on said solid support and mixing said starch and said support with a modifying agent selected from a group consisting of: an aliphatic dihalide, an epoxyhalogen, and an aliphatic diamine to increase the affinity of said starch for said support.

2. The method of claim 1 wherein said epoxyhalogen is epichlorohydrin.

3. The method of claim 1 wherein said solid support is a refractory oxide.

4. The method of claim 3 wherein said refractory oxide is alumina.

5. The method of claim 1 wherein said starch is amylose.

6. The method of claim 1 wherein said enzyme is dextranase.

7. The method of claim 1 wherein said aliphatic dihalide is dibromoethane.

8. The method of claim 1 wherein said aliphatic diamine is diaminopropane.

* * * * *